(12) United States Patent
Utsunomiya et al.

(10) Patent No.: US 10,520,479 B2
(45) Date of Patent: Dec. 31, 2019

(54) LIQUID CHROMATOGRAPH MASS SPECTROMETER

(71) Applicant: SHIMADZU CORPORATION, Kyoto-shi, Kyoto (JP)

(72) Inventors: Shinichi Utsunomiya, Kyoto (JP); Yusaku Hioki, Nagahama (JP); Yuki Ohta, Kawasaki (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 405 days.

(21) Appl. No.: 14/479,874

(22) Filed: Sep. 8, 2014

(65) Prior Publication Data

US 2016/0069848 A1    Mar. 10, 2016

(51) Int. Cl.
*G01N 30/86* (2006.01)
*G01N 30/02* (2006.01)
(Continued)

(52) U.S. Cl.
CPC ..... *G01N 30/8658* (2013.01); *G01N 30/7233* (2013.01); *G01N 30/463* (2013.01);
(Continued)

(58) Field of Classification Search
CPC ...................................................... G01N 30/72
See application file for complete search history.

(56) References Cited

U.S. PATENT DOCUMENTS 4,042,327 A * 8/1977 Haney .................. G01N 30/48
210/656

2006/0027490 A1 * 2/2006 DeMarco ............... G01N 30/88
210/198.2

(Continued)

FOREIGN PATENT DOCUMENTS

JP    200-214151    8/2000
JP    2004-184149    7/2004
(Continued)

OTHER PUBLICATIONS

March, Raymond E. "An introduction to quadrupole ion trap mass spectrometry." Journal of mass spectrometry 32.4 (1997): 351-369.*

(Continued)

*Primary Examiner* — Herbert K Roberts
(74) *Attorney, Agent, or Firm* — Sughrue Mion, PLLC

(57) ABSTRACT

In a liquid chromatograph mass spectrometer (LC/MS) for performing mass spectrometry of fractionated samples prepared with a multi-dimensional LC or similar LC with high separatory capability, fractionated sample useful information which shows the degree of usefulness of various substances with respect to retention time is prepared from prior information which includes, for example, elution characteristics in the LC depending on the kind of column or other factors or the degree of ease of ionization in the MS. During a measurement, the preparative separation of an eluate and the preparation of fractionated samples are not performed within a period of time which has been judged to be useless based on the fractionated sample useful information. By selecting fractionated samples at each dimension of the multi-dimensional LC, the number of fractionated samples to be eventually subjected to mass spectrometry can be significantly reduced.

8 Claims, 5 Drawing Sheets

(51) Int. Cl.
  *G01N 30/46*  (2006.01)
  *G01N 30/72*  (2006.01)
  *H01J 49/16*  (2006.01)
  *G01N 30/84*  (2006.01)
  *G01N 30/88*  (2006.01)

(52) U.S. Cl.
  CPC .............. *G01N 2030/8411* (2013.01); *G01N 2030/8831* (2013.01); *H01J 49/164* (2013.01)

(56) References Cited

U.S. PATENT DOCUMENTS

2006/0118713 A1*  6/2006  Matsui ............... G01N 30/7266
                                                        250/288
2011/0184648 A1*  7/2011  Gorenstein ............ G01N 30/72
                                                        702/19

FOREIGN PATENT DOCUMENTS

| JP | 2007-503594 | 2/2007 | |
| JP | 2007-163435 | 6/2007 | |
| JP | 2007163435 A * | 6/2007 | ............ G01N 30/80 |
| JP | 2010-014559 | 1/2010 | |
| WO | 2004/106915 | 12/2004 | |

OTHER PUBLICATIONS

Asperger, et al., "A new high capacity MALDI target format for improved LC-MALDI analysis of compex proteomics samples", ASMS Conf., 2011.

Iwasaki, et al., "One-Dimensional Capillary Liquid Chromatographic Separation Coupled with Tandem Mass Spectrometry Unveils the *Escherichia coli* Proteome on a Microarray Scale", Analytical Chemistry, 2010, vol. 82, pp. 2616-2620.

Horvatovich, et al., "Multidimensional chromatography coupled to mass spectrometry in analysing complex proteomics samples", J Sep. Sci.; 2010, vol. 33; pp. 1421-1437.

Fournier, et al., "Multidimensional Separations-Based Shotgun Proteomics", Chem. Rev., 2007, vol. 107, 3654-3686.

Japanese Office Action dated Sep. 15, 2015 in corresponding Japanese Patent Application No. 2012-042960.

* cited by examiner

Fig. 3A WHEN RP COLUMN IS USED
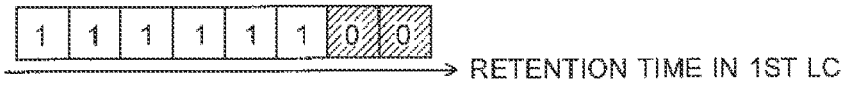
→ RETENTION TIME IN 1ST LC
Fig. 3B WHEN HILIC COLUMN IS USED
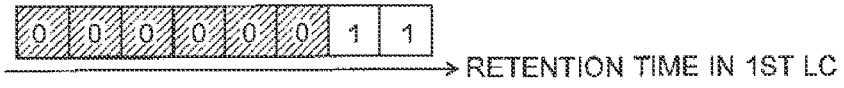
→ RETENTION TIME IN 1ST LC
Fig. 4A
WHEN RP COLUMN IS USED IN 1ST LC AND SCX COLUMN IN 2ND LC
RETENTION TIME IN 2ND LC
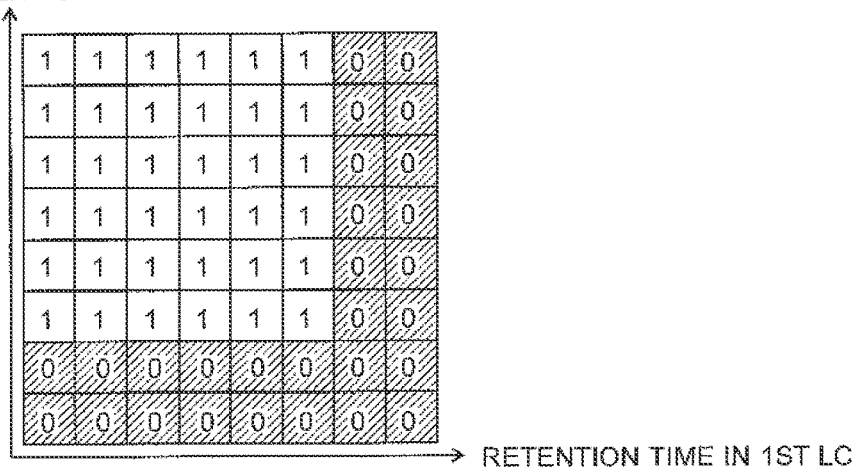
→ RETENTION TIME IN 1ST LC
Fig. 4B
WHEN HILIC COLUMN IS USED IN 1ST LC AND SCX COLUMN IN 2ND LC
RETENTION TIME IN 2ND LC
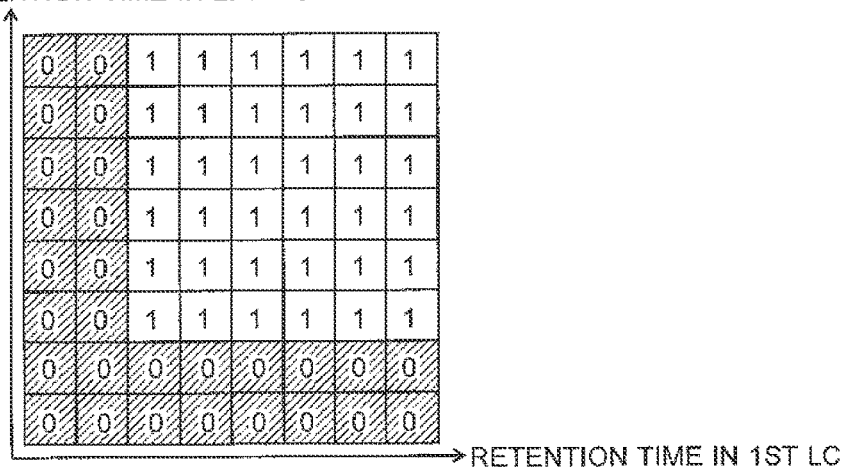
→ RETENTION TIME IN 1ST LC

Fig. 6

| Sample | | | Liquid Chromatography | | Mass Spectrometry | Method of Excluding Fractionated Samples |
|---|---|---|---|---|---|---|
| | | | Separation Mode | Elution Characteristics | Ionization Characteristics | |
| Water-Soluble | Ionic | | Cation Exchange | Acidic Substance -> Basic Substance | | Exclude Initial Phase of Retention Time |
| | | | Anion Exchange | Basic Substance -> Acidic Substance | | Exclude Last Phase of Retention Time |
| | | | Ion Pair | Hydrophilic Substance -> Hydrophobic Substance | | Exclude Last Phase of Retention Time |
| | | | Size Exclusion | High Molecular Weight -> Low Molecular Weight | | Exclude Initial Phase of Retention Time |
| | | | Size Exclusion | High Molecular Weight -> Low Molecular Weight | | Exclude Initial Phase of Retention Time |
| | | | Hydrophilic Interaction | Hydrophobic Substance -> Hydrophilic Substance | Substances Having the Following Properties are More Difficult to Ionize: Acidic Substance <-- Hydrophobic <-- High Molecular Weight <-- | Exclude Initial Phase of Retention Time |
| | | | Reverse Phase | Hydrophilic Substance -> Hydrophobic Substance | | Exclude Last Phase of Retention Time |
| | Non-Ionic | | Reverse Phase | Hydrophilic Substance -> Hydrophobic Substance | | Exclude Last Phase of Retention Time |
| | | | Normal Phase | Hydrophobic Substance -> Hydrophilic Substance | | Exclude Initial Phase of Retention Time |
| Soluble in Organic Solvent | | | Normal Phase | Hydrophobic Substance -> Hydrophilic Substance | | Exclude Initial Phase of Retention Time |
| | | | | High Molecular Weight -> Low Molecular Weight | | |
| | | | Size Exclusion | High Molecular Weight -> Low Molecular Weight | | Exclude Initial Phase of Retention Time |

LIQUID CHROMATOGRAPH MASS SPECTROMETER

TECHNICAL FIELD

The present invention relates to a liquid chromatograph mass spectrometer (LC/MS) consisting of a liquid chromatograph (LC) coupled with a mass spectrometer (MS), and more specifically, to a liquid chromatograph mass spectrometer suitable for a multi-dimensional LC/MALDI-MS in which a plurality of samples fractionated by multi-dimensional liquid chromatography are ionized by a matrix assisted laser desorption ionization (MALDI) source and subjected to mass spectrometry.

BACKGROUND ART

In bioscience research, medical treatment, drug development and similar fields, it has become increasingly important to examine biological samples to comprehensively identify various substances, such as proteins, peptides, nucleic acids and sugar chains. In particular, when aimed at proteins or peptides, such a comprehensive analysis method is called "shotgun proteomics." For such analyses, the combination of a liquid chromatography and an $MS^n$ mass spectrometer (tandem mass spectrometer) has proven itself to be a very powerful technique.

As a mass spectrometer used for the previously described purposes (any type of mass spectrometer, including an $MS^n$ mass spectrometer, is hereinafter simply called the mass spectrometer), an ESI-MS having an electrospray ionization (ESI) source or a MALDI-MS having a MALDI ion source is used. In the case of an LC/ESI-MS, i.e. the combination of an LC and an ESI-MS, since the components in a liquid sample can be directly ionized, the introduction of the sample from the LC into the MS has been automatized. By contrast, the LC/MALDI-MS, i.e. the combination of an LC and a MALDI-MS, requires a larger amount of workload of analysis operators than the LC/ESI-MS since it requires the task of preparative-separating and fractionating sample components separated by the LC and placing spots of fractionated samples onto a sample plate. The workload for such a task can be reduced, for example, by using an automatic sample-dropping device described in Patent Literature 1.

For a comprehensive analysis of biological samples containing a number of components and having a wide dynamic range (i.e. with a wide range of component concentrations), it is necessary to achieve a high level of separatory capability in the LC. Attempts have been made for that purpose, such as a multi-dimensional separation using various separation modes combined together (see Non-Patent literatures 1 and 2) or a prolonged analysis using a meter-long monolithic silica column (see Non-Patent Literature 3). By using such LC techniques with high levels of separatory capability, the number of components contained in each fractionated sample can be reduced and a high-quality mass spectrum with a smaller amount of noise factors can be obtained. However, a problem exists in that a large number of fractionated samples need to be prepared, so that the analytical measurement time (i.e. the period of time for performing a mass spectrometry of the fractionated samples and collecting data) will be long. Furthermore, since an enormous amount of mass spectrum data are obtained through the mass spectrometry, an extremely long period of time is required for the data analysis. In particular, in the case of the LC/MALDI-MS, which has the LC and the MALDI-MS connected offline, an increase in the number of fractionated samples to be individually placed on a sample plate almost directly leads to an increase in the entire analysis time (see Non-Patent Literature 4).

Therefore, although a high level of LC-separatory capability has been achieved, it is inevitable to limit the number of fractionations taking into account the limitation of the analytical measurement time and the data analysis time. As a result, a plurality of components (in particular, an impurity that is unrelated to the analysis) may be mixed in one fractionated sample, which lowers the accuracy of the analysis.

In a system described in Patent Literature 2, the enormous amount of data obtained by an LC/MS or LC/MS/MS analysis is reduced to a smaller amount of data before an analyzing process in such a manner that the data which can be regarded as originating from a known sample yet being out of interest are removed based on the retention time in the LC, the mass value in the MS and/or other clues, leaving only such data that possibly contain new findings. This technique can reduce the amount of data to be analyzed but cannot shorten the period of time required for the original analytical measurement. There also remains the problem that the enormous amount of data collected through the analysis need to be temporarily stored in a memory or other storage devices and it is necessary to ensure a sufficient memory capacity for that purpose.

CITATION LIST

Patent Literature

Patent Literature 1: JP 2004-184149 A
Patent Literature 2: JP 2007-503594 A

Non Patent Literature

Non Patent Literature 1: Fournier M L et al., "Multidimensional separations-based shotgun proteomics", Chem. Rev., 2007, 107(8), pp. 3654-3686

Non Patent Literature 2: Horvatovich P. et al., "Multidimensional chromatography coupled to mass spectrometry in analysing complex proteomics samples", J Sep Sci., 2010, 33(10), pp. 1421-1437

Non Patent Literature 3: Iwasaki M. et al., "One-dimensional capillary liquid chromatographic separation coupled with tandem mass spectrometry unveils the *Escherichia coli* proteome on a microarray scale", Anal Chem., 2010, 82(7), pp. 2616-2620

Non Patent Literature 4: Arndt Asperger et al., "A new high capacity MALDI target format for improved LC-MALDI analysis of complex proteomics samples", ASMS Conf., 2011, WP629

SUMMARY OF INVENTION

Technical Problem

The present invention has been developed to solve the previously described problem. Its objective is to provide a liquid chromatograph mass spectrometer for performing a mass spectrometry of each of a plurality of samples fractionated into small quantities using an LC with a meter-long column, a multi-dimensional LC or other techniques, the liquid chromatograph mass spectrometer being designed so that the measurement time and the analysis time can be shortened and the amount of data to be collected can be reduced.

Another objective of the present invention is to provide a liquid chromatograph mass spectrometer in which unnecessary information contained in mass spectrum data can be prevented from disturbing an analysis based on the mass spectrum data and a decrease in the accuracy of the analysis can be avoided.

Solution to Problem

The first aspect of the present invention aimed at solving the previously described problem is a liquid chromatograph mass spectrometer having a liquid chromatograph for temporally separating various substances contained in a sample and a mass spectrometer for performing a mass spectrometry for each of a plurality of fractionated samples corresponding to different retention times obtained by fractionating the sample separated into components by the liquid chromatograph, the liquid chromatograph mass spectrometer including:

a) a fractionated sample usefulness information memory for holding fractionated sample usefulness information previously defined corresponding to an analysis condition;

b) an analysis condition setter for allowing an analysis operator to set an analysis condition in advance of an execution of an analysis; and c) a controller for retrieving, from the fractionated sample usefulness information memory, the fractionated sample usefulness information corresponding to the analysis condition set through the analysis condition setter and for controlling a fractionating operation, based on the fractionated sample usefulness information, so that only substances with high degrees of usefulness are contained in the fractionated samples.

In the first aspect of the present invention, the process of "controlling a fractionating operation . . . so that only substances with high degrees of usefulness are included in the fractionated samples" means controlling the fractionating operation so that substantially all the substances contained in the fractionated samples have high degrees of usefulness. This does not exclude the case where the fractionating operation is performed in such a manner that substances with relatively low degrees of substances are contained in a portion of the fractionated samples, provided that the number of fractionated samples does not extremely increase, i.e. provided that time allows it or the thereby caused increase in the workload of the analysis operator is allowable.

The second aspect of the present invention aimed at solving the previously described problem is a liquid chromatograph mass spectrometer having a liquid chromatograph for temporally separating various substances contained in a sample and a mass spectrometer for performing a mass spectrometry for each of a plurality of fractionated samples corresponding to different retention times obtained by fractionating the sample separated into components by the liquid chromatograph, the liquid chromatograph mass spectrometer including:

a) a fractionated sample usefulness information memory for holding fractionated sample usefulness information previously defined corresponding to an analysis condition;

b) an analysis condition setter for allowing an analysis operator to set an analysis condition in advance of an execution of an analysis; and c) a controller for retrieving, from the fractionated sample usefulness information memory, the fractionated sample usefulness information corresponding to the analysis condition set through the analysis condition setter and for controlling a fractionating operation so as to change the duration of fractionation based on the fractionated sample usefulness information.

In general, the fractionated sample usefulness information is defined based on prior information which has been experimentally or theoretically known. The "prior information" is, for example, a set of known information about the relationship between the elution (separation) characteristics and the sample properties and/or the separation mode (e.g. the kind of column), or the relationship between the degree of ease of ionization and the kind of ion source in the mass spectrometer and/or the substance properties. The fractionated sample usefulness information is a set of information which is previously defined according to the analysis condition, based on the prior information, and taking into account additional judgments about other factors, such as whether or not the analysis performed by the mass spectrometer will be reliable or valid, or whether or not information useful for the purpose of the analysis will be obtained through an analysis of the measured result.

As one specific example of the prior information, it is known that, when the mass spectrometer uses an ion source which ionizes a sample by MALDI or ESI, the ionization is more difficult for a substance which is more acidic, which is more hydrophobic or which has a higher molecular weight. Another example of the prior information is the knowledge on how the kind of substance which is more quickly eluted in the liquid chromatograph changes depending on the sample properties and/or the separation mode. Accordingly, in some cases, it is possible to determine, for a substance which is difficult to ionize, that the result of a measurement of this substance using the mass spectrometer is low in reliability and validity, and analyzing the measurement result is practically useless. When such an additional judgment is made, it is possible to prepare fractionated sample usefulness information which states that the degree of usefulness of the fractionated sample is low at retention times when acidic, hydrophobic or high-molecular weight substances are eluted while the degree of usefulness is high at retention times when substances having opposite characteristics (basic, hydrophilic or low-molecular weight substances) are eluted. The prepared information is stored in the fractionated sample usefulness information memory.

For example, the fractionated sample usefulness information may be information showing a temporal change of an index value representing the degree of usefulness with respect to the retention time. The index value may be binary information corresponding to whether or not the sample is useful, or it may be multi-level information indicating the level of usefulness.

Although the fractionated sample usefulness information may be prepared on the user's side, it is generally preferable to have the manufacturer prepare the information and store it in a storage device before delivering the system to the user. It is also possible to add or update information in the storage device through a version upgrade or similar process after the delivery of the system to the user.

In the liquid chromatograph mass spectrometer according to the first aspect of the present invention, when an analysis is performed according to an analysis condition which has been set through the analysis condition setter, the controller retrieves, from the fractionated sample usefulness information memory, fractionated sample usefulness information corresponding to that analysis condition and appropriately controls the fractionating operation based on this information, for example, in such a manner that the sample is preparative-separated and fractionated during the period of time when a substance with a high degree of usefulness is eluted in the liquid chromatograph while the sample is not preparative-separated during the period of time when a substance with a relatively low degree of usefulness is eluted. Every fractionated sample thus prepared contains a highly useful substance. As a result, the number of fractionated samples to be prepared is dramatically reduced as compared to the conventional case where all kinds of substances are preparative-separated and fractionated regardless of their usefulness.

In the liquid chromatograph mass spectrometer according to the second aspect of the present invention, when an analysis is performed according to an analysis condition which has been set through the analysis condition setter, the controller retrieves, from the fractionated sample usefulness information memory, fractionated sample usefulness information corresponding to that analysis condition and controls the fractionating operation based on this information, for example, in such a manner that the duration of each fractionation is decreased during the period of time when a substance with a high degree of usefulness is eluted in the liquid chromatograph while the duration of each fractionation is increased during the period of time when a substance with a relatively low degree of usefulness is eluted. With this system, it is possible to dramatically reduce the number of fractionated samples to be prepared as compared to the conventional case, while making best efforts to prevent each of the useful substances from being mixed with other substances in the same fractionated sample.

In a preferable mode of the liquid chromatograph mass spectrometer according to the first or second aspect of the present invention, the liquid chromatograph is a multi-dimensional liquid chromatograph capable of multi-dimensional separation and fractionation, the fractionated sample usefulness information is prepared for each dimension of the liquid chromatograph, and the controller is configured so as to control the fractionating operation based on the fractionated sample usefulness information corresponding to the analysis condition so that substances with high degrees of usefulness are contained in the fractionated samples prepared in each dimension of the liquid chromatograph while preventing substances with relatively low degrees of usefulness from being contained in any of the fractionated samples, or so as to control the fractionating operation based on the fractionated sample usefulness information so that the duration of fractionation for a comparatively useful substance is decreased in each dimension of the liquid chromatograph.

Advantageous Effects of the Invention

With the liquid chromatograph mass spectrometer according to the first or second aspect of the present invention, while ensuring the correctness and the reliability of an analysis result according to the purpose of the analysis, the number of fractionated samples to be subjected to mass spectrometry can be reduced so as to shorten the analytical measurement time for collecting data and the period of time for analyzing the data obtained through the measurement, and thereby improve the throughput of the analysis. This effect is particularly noticeable in a liquid chromatograph mass spectrometer using a MALDI-MS, which requires analysis operators to perform burdensome tasks and operations. In the case of the previously described configuration using a multi-dimensional liquid chromatograph, the number of fractionated samples can be decreased stepwise for each dimension of the liquid chromatograph, so that the effect of reducing the analytical measurement time is even more noticeable as compared to the case where a normal (one-dimensional) liquid chromatograph is used.

Another advantage of the liquid chromatograph mass spectrometer according to the first or second aspect of the present invention is that the capacity of the memory device for storing data can be saved since the amount of data collected with the mass spectrometer is decreased. The liquid chromatograph mass spectrometer according to the first aspect of the present invention has still another advantage that the data which are useless for mass spectrum data to be obtained (e.g. the data originating from impurities) are significantly reduced and the analysis is less disturbed by such unwanted information, so that the accuracy of the analysis is improved.

BRIEF DESCRIPTION OF DRAWINGS

FIGS. 3A and 3B are examples of the fractionated sample usefulness information in a first LC.

FIGS. 4A and 4B are examples of the fractionated sample usefulness information in a two-dimensional LC.

FIG. 6 is one example of the relationship between prior information and the judgment on the usefulness of fractionated samples.

DESCRIPTION OF EMBODIMENTS

Figure 1:
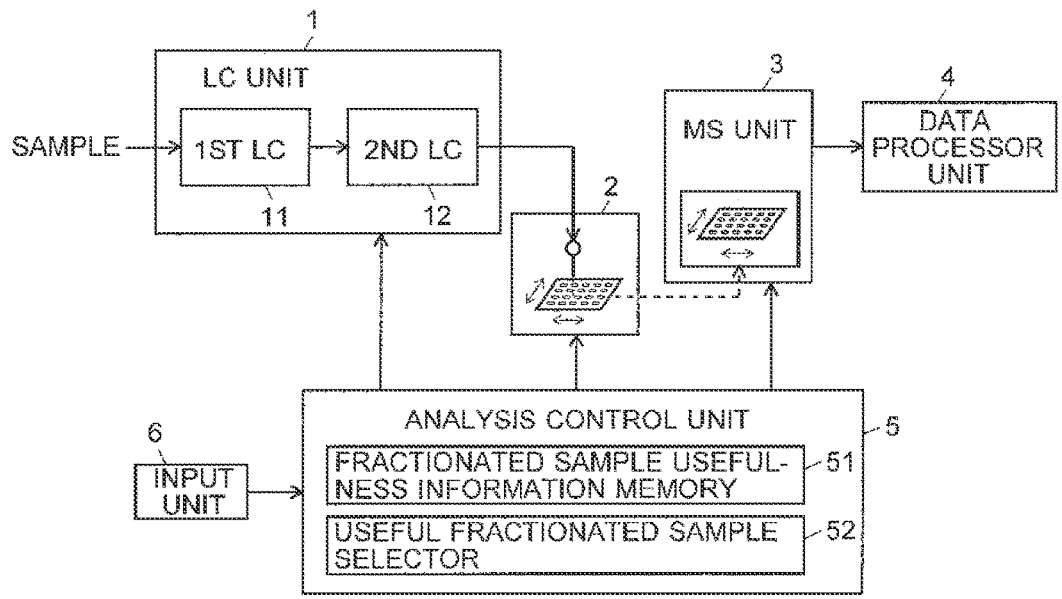
FIG. 1 is a schematic configuration diagram of a two-dimensional LC/MALDI-MS according to one embodiment of the present invention.

A two-dimensional LC/MALDI-MS as one embodiment of the present invention is hereinafter described with reference to the attached drawings. FIG. 1 is a schematic configuration diagram of a two-dimensional LC/MALDI-MS according to the present embodiment.

The two-dimensional LC/MALDI-MS of the present embodiment includes an LC unit 1 for separating various kinds of substances in a liquid sample according to their retention times, a preparative separation and fractionation unit 2 for preparative-separating and fractionating a sample containing the substances separated by the LC unit 1 to prepare a plurality of fractionated samples containing different substances, an MS unit 3 for sequentially performing a mass spectrometry (an $MS^1$ analysis or $MS^n$ analysis with n being an integer equal to or greater than two) on the fractionated samples, a data processing unit 4 for processing data obtained with the MS unit 3, an analysis control unit 5 for controlling the operations of the LC unit 1, the preparative separation and fractionation unit 2 and the MS unit 3 so as to collect data, and an input unit 6 for setting analysis conditions and other information.

The LC unit 1 is a two-dimensional LC including a first LC 11 and a second LC 12. The liquid sample containing various kinds of substances separated by the first LC 11 according to their retention times is divided into fractions, which are individually and temporarily held in a trap. Subsequently, the fractionated samples held in the trap are introduced into the second LC 12 and eluted after being separated according to their retention times. The preparative separation and fractionation unit 2 fractionates the eluate at preset intervals of time and sequentially drops the fractions of the eluate into different wells formed on a MALDI sample plate. Thus, a fractionated sample is prepared in each well. The MS unit 3 (for example, a MALDI-TOFMS) sequentially performs a mass spectrometry on each of the fractionated samples prepared in the wells on the sample plate and collects mass spectrum data. That is to say, the MS unit 3 repeats the mass spectrometry as many times as the number of fractionated samples prepared on the sample plate.

The analysis controller 5 includes a fractionated sample usefulness information memory 51 in which fractionated sample usefulness information (which will be described later) is stored beforehand, and a useful fractionated sample selector 52 for selecting fractionated samples based on the information. The functions of the data processor unit 4 and the analysis control unit 5 can partially or entirely be realized, for example, by installing a dedicated controlling and processing software program on a personal computer provided as hardware resources and executing the program on the same computer.

The fractionated sample usefulness information stored in the fractionated sample usefulness information memory 51 is hereinafter described. FIG. 6 shows one example of the relationship between prior information (which serves as a basis for creating fractionated sample usefulness information) and the usefulness of fractionated samples.

As shown, the prior information used in the present embodiment includes information that can influence separation characteristics in liquid chromatography such as, information about the relationship between sample properties as well as analysis conditions and elution characteristics, where the "analysis conditions" include the kind of separation mode (the kind of column; more specifically, the kind of column-packing material, the inner diameter of the column, the length of the column and so on), the kind of mobile phase used, and other factors which can influence separation characteristics in liquid chromatography, that is, the relationship between the kind of substance (e.g. acidic, basic, hydrophilic, hydrophobic, low-molecular weight, or high-molecular weight substances) and the degree of ease of elution. The prior information also includes information about the relationship between the kind of ion source used in the mass spectrometer and the ionization characteristics (i.e. the degree of ease of ionization). It is preferable to additionally take into account other analysis conditions related to the liquid chromatography, such as the column temperature, gradient characteristics, the kind (composition) of mobile phase, the flow rate of the mobile phase, the kind of sample solvent, the amount of injection of the sample, or the kind of ion-pair reagent.

For example, when peptides are separated by liquid chromatography using a reverse-phase column, hydrophilic peptides are initially eluted, which are followed by hydrophobic peptides, where, for example, the elution times of hydrophobic peptides (which are difficult to be ionized by MALDI ion sources) can be predicted by calculation. When the liquid chromatography is performed using a cation-exchange resin, acidic peptides are initially eluted, which are followed by basic peptides, where, for example, the basic peptides containing arginine, lysine or other kinds of amino acids which are easily ionized by MALDI ion sources are known to be eluted at later points in time.

A substance which is difficult to ionize in the ion source of the mass spectrometer ("hard-to-ionize substance") produces a relatively small amount of ions to be subjected to mass spectrometry and is likely to be analyzed with low sensitivity or be almost undetectable. Accordingly, it is possible to judge hard-to-ionize substances to be less useful. Based on this judgment, it can be considered as less meaningful to collect an eluate during the period of time when a substance which is difficult to ionize for the given elution characteristics of the LC is eluted, while it is highly meaningful to collect the eluate, i.e. to prepare fractionated samples, during the period of time when a substance which can be easily ionized is eluted. Accordingly, the fractionated sample usefulness information which shows the degree of usefulness with respect to the retention time is created in such a manner that the value "useful" is shown for a period of time when it is probably meaningful to prepare fractionated samples and the value "useless" is shown for a period of time when it is probably less meaningful to prepare fractionated samples.

As the simplest form of the fractionated sample usefulness information, the values "1" and "0" can be assigned to the "useful" and "useless" periods of time, respectively, with respect to the retention time. FIGS. 3A and 3B show one example of the fractionated sample usefulness information for the first LC, where FIG. 3A is the case of using a reverse-phase (RP) column and FIG. 3B is the case of using a hydrophilic interaction (HILIC) column. The horizontal axis is the retention time (elution time), where each segment in the horizontal direction can be regarded as indicative of an arbitrary duration. According to the present fractionated sample usefulness information, for example, if the analysis is performed using a reverse-phase column, the analysis is "useful" from the first to sixth segments of time appearing with the lapse of time, while the analysis is "useless" in the subsequent segments.

In the case of a multi-dimensional LC, the one-dimensional information extending along one time axis as shown in FIGS. 3A and 3B is expanded into a multi-dimensional form. FIGS. 4A and 4B show one example of the fractionated sample usefulness information for a two-dimensional LC. The horizontal axis is similar to FIGS. 3A and 3B and shows the retention time in the first LC, while the vertical axis shows the retention time in the second LC. The meanings of the values "1" and "0" are the same as in FIGS. 3A and 3B. In the case of FIG. 4A, the reverse-phase column as shown in FIG. 3A is used as the first LC and a strong cation-exchange (SCX) column is used as the second LC. In the case of FIG. 4B, the hydrophilic interaction column as shown in FIG. 3B is used as the first LC and a strong cation-exchange column is used as the second LC. As shown, the first and second LCs in a two-dimensional LC normally have different separation characteristics. It should be noted that the examples shown in FIGS. 3A through 4B are simplified for ease of explanation in which only the separation mode in the liquid chromatography and the degree of ease of ionization in the ion source of the mass spectrometer are considered as the analysis conditions. If other analysis conditions as mentioned earlier are also taken into account, a set of fractionated sample usefulness information as shown in FIGS. 3A through 4B is obtained for each combination of the various analysis conditions.

Basically, the task of preparing fractionated sample usefulness information from experimentally or theoretically obtained prior information and storing the information in the memory 51 of the system is performed on the manufacturer's side before the system is delivered to the user. However, it is preferable to provide the function of appropriately updating the data in the fractionated sample usefulness information memory 51, taking into account the fact that new analysis conditions may be added in the future as a result of the development of a new separation mode or for other reasons. Naturally, it is also possible to provide a means for allowing users to add or modify fractionated sample usefulness information.

Figure 2:
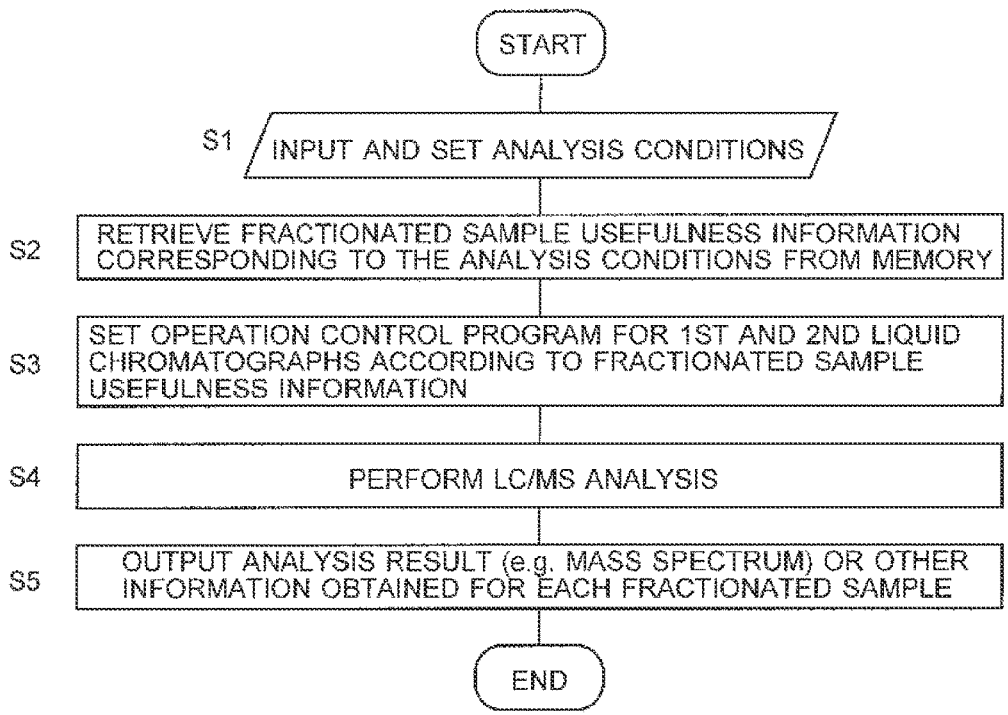
FIG. 2 is a flowchart showing an analysis procedure in the two-dimensional LC/MALDI-MS of the present embodiment.
Figure 5:
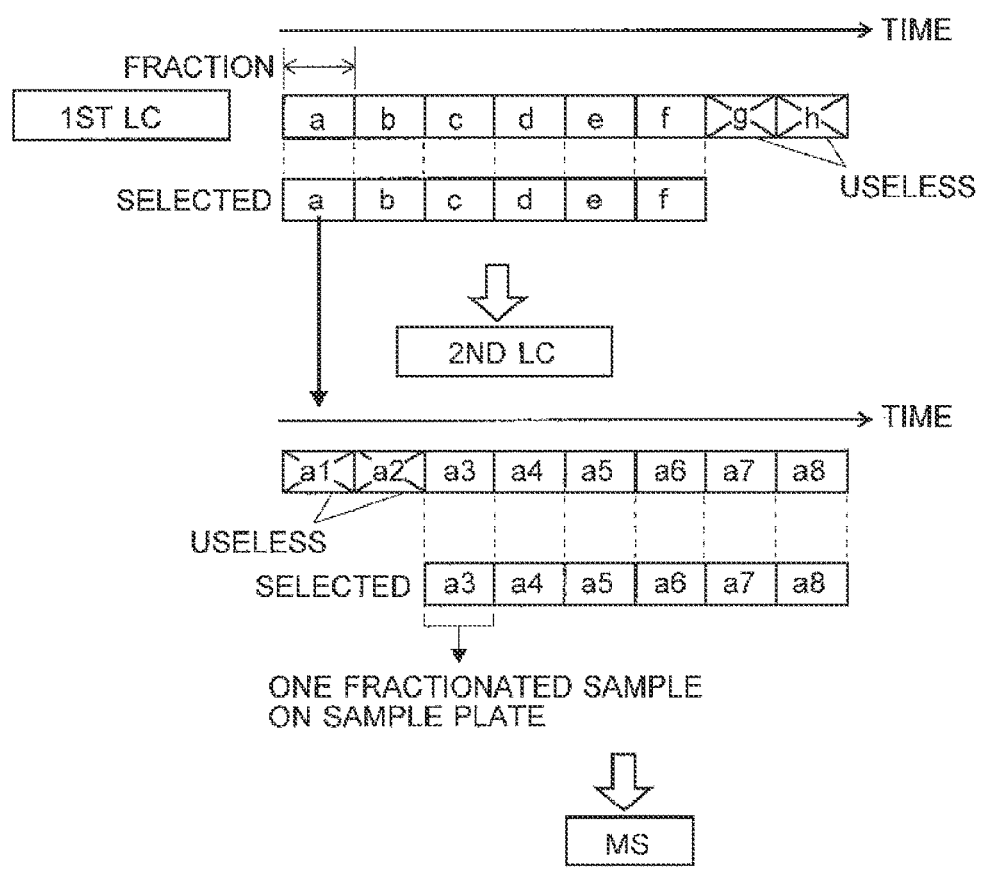
FIG. 5 is a conceptual diagram showing the operation of selecting fractionated samples using the fractionated sample usefulness information shown in FIG. 4A.

One example of the analysis in the two-dimensional LC/MALDI-MS of the present embodiment is hereinafter described with reference to FIGS. 2 and 5. FIG. 2 is a flowchart showing an analysis procedure in the two-dimensional LC/MALDI-MS of the present embodiment. FIG. 5 is a conceptual diagram showing the operation of selecting fractionated samples using the fractionated sample usefulness information shown in FIG. 4A.

Initially, an analysis operator inputs and sets various analysis conditions through the input unit 6 (Step S1). It is not always necessary for the analysis operator to manually input all the previously mentioned analysis conditions used in the LC unit 1 and the MS unit 3. This is because a portion of the analysis conditions may be previously set by default, in which case the input and setting needs to be performed only when the conditions need to be changed. Furthermore, if the system has a built-in function for automatically determining the kind of installed column or other system configurations, a portion of the analysis conditions can be automatically set without requiring the analysis operator to make inputs.

After the analysis conditions are fixed, the useful fractionated sample selector 52 in the analysis controller 5 retrieves, from the fractionated sample usefulness information memory 51, the fractionated sample usefulness information corresponding to the combination of the analysis conditions (Step S2). As one example, it is hereinafter assumed that the kind of column is the only analysis condition to be considered in selecting the fractionated sample usefulness information, and that the fractionated sample useful information as shown in FIGS. 3A and 4A has been retrieved. Based on the fractionated sample useful information thus retrieved, the useful fractionated sample selector 52 configures an operation control program for controlling the preparative separation and fractionation in the first LC 11 as well as the preparative separation and fractionation of an eluate from the second LC 12 in the preparative separation and fractionation unit 2 (Step S3). More specifically, the operation control program for the first LC 11 is created based on the fractionated sample usefulness information shown in FIG. 3A so that the preparative separation and fractionation is not performed in the last phase of the retention time which has been judged to be "useless", while the operation control program for the preparative separation and fractionation unit 2 is created based on the fractionated sample usefulness information shown in FIG. 4A so that the preparative separation and fractionation is not performed in the initial phase of the retention time which has been judged to be "useless."

Subsequently, the analysis controller 5 conducts an LC/MS analysis by controlling the LC unit 1, the preparative separation and fractionation unit 2 and the MS unit 3 (Step S4). Various components contained in the sample introduced into the first LC 11 are separated according to their retention times. The eluate from the reverse-phase column (not shown) in the first LC 11 is preparative-separated and fractionated for each predetermined duration of fractionation. However, according to the previously described operation control program, the eluate obtained in the last phase of the retention time is disposed and not preparative-fractionated. In the example of FIG. 5, only six fractionated samples "a" through "f" are prepared while the last two fractionated samples "g" and "h" are disposed, unlike the conventional case in which all the eight samples "a" through "h" are prepared. Each of the six fractionated samples is individually introduced into the second LC 12, in which the sample is further separated into various substances according to their retention times. For example, consider the case where the fractionated sample "a" is separated in the second LC 12 and eluted. If a conventional system is used, eight fractionated samples "a1" through "a8" are prepared from this eluate. By contrast, in the preparative separation and fractionation unit 2 of the present system, which operates according to the previously described control program, the eluate obtained in the initial phase of the retention time is disposed and not preparative-separated. As a result, the portion of the eluate corresponding to "a1" and "a2" is disposed, while six fractionated samples "a3" through "a8" are prepared on the sample plate. Five other fractionated samples "b" through "f" prepared in the first LC 11 are also processed in the same manner.

That is to say, in the conventional case, eight fractionated samples are initially prepared in the first LC 11, and eight fractionated samples are prepared from each of the initially prepared samples in the second LC 12 and the preparative separation and fractionation unit 2, so that a total of 64 fractionated samples are eventually prepared and subjected to mass spectrometry in the MS unit 3. By contrast, in the two-dimensional LC/MALDI-MS of the present embodiment, six fractionated samples are initially prepared in the first LC 11, and six fractionated samples are prepared from each of the initially prepared samples in the second LC 12 and the preparative separation and fractionation unit 2, with a total of 36 fractionated samples to be subjected to mass spectrometry in the MS unit 3. The decrease in the number of fractionated samples does not lead to a substantial decrease in the amount of information, since the portions of the eluate which are disposed in the LCs 11 and 12 contain relatively useless substances which are unlikely to produce useful signals if subjected to the mass spectrometry.

The MS unit 3 performs a mass spectrometry on each of the fractionated samples prepared on the sample plate. The data processor unit 4 creates a mass spectrum or other kinds of information based on the data obtained from each fractionated sample and outputs the information as an analysis result (Step S5). The previously described decrease in the number of fractionated samples to be analyzed in the MS unit 3 leads to a significant decrease in the period of time required for the mass spectrometry in the MS unit 3. The amount of data obtained by the analysis is also reduced, which allows a reduction in the memory capacity for storing the data.

In the example of FIG. 5, a reverse-phase column is used in the first LC 11 and a strong cation-exchange (SCX) column is used in the second LC 12. If a hydrophilic interaction column is used in the first LC 11 and a strong cation-exchange column is used in the second LC 12, the fractionated sample usefulness information for the second LC 12 will be as shown in FIG. 4B, in which case the portion of the eluate corresponding to fractionated samples "a" and "b" is disposed and only six fractionated samples "c" through "h" are prepared in the first LC 11. The other points are the same as described in the previous embodiment.

Figure 7:
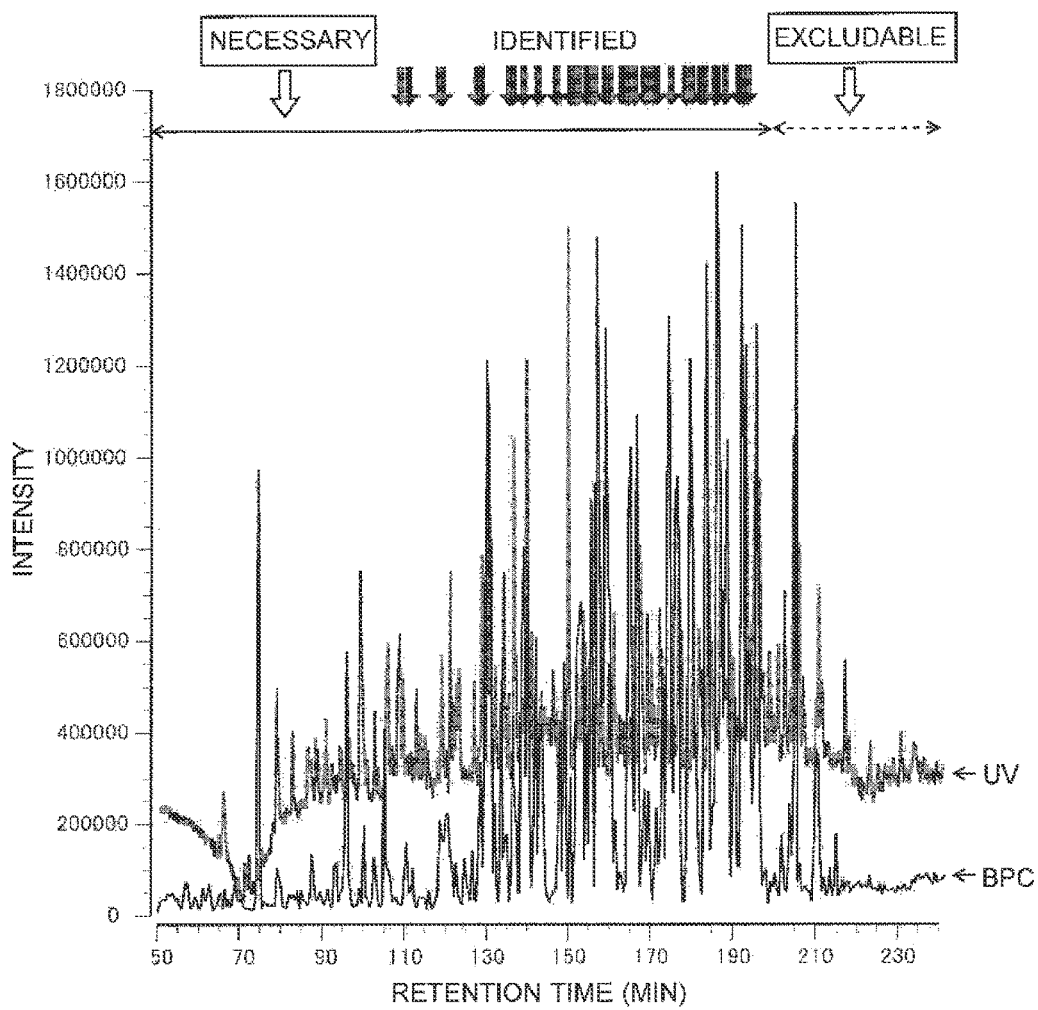
FIG. 7 is a chromatogram (total ion chromatogram) actually obtained with a reverse-phase LC/MALDI-MS.

FIG. 7 shows one example of the data obtained through actual measurements in which various substances separated by an LC using a reverse-phase column were analyzed with an ultraviolet visible spectrometric detector (UV) and a MALDI-MS (BPC=Base Peak Chromatogram in FIG. 7). In both chromatograms UV and BPC, in which the acquired data include all the substances in the eluate, almost no information necessary for identifying the substances can be found in the last phase of the retention time. Fractionated samples obtained within such a range of retention time are useless and can be excluded before being transferred to the LC or MS unit in the next stage.

In the previous embodiment, the present invention is applied in a two-dimensional LC/MALDI-MS. It is evident that the number of dimensions of the LC is not limited to "two." Although an increase in the number of dimensions makes the control more complex, the overall effect of decreasing the analytical measurement time and the amount of data will be more noticeable, since the number of fractionated samples can be reduced in each dimension of the LC.

In the previous embodiment, the fractionated sample usefulness information is binary information corresponding to whether or not the sample is useful. It may be multi-value information indicating the level of usefulness. For example, the usefulness information may be a continuous value ranging from 0 to 100, with the value of 0 meaning that there is no usefulness and the value of 100 meaning that the usefulness is extremely high. With this system, whether or not a given fractionated sample should be adopted can be determined by comparing its usefulness value with a threshold. Changing this threshold leads to a change in the number of fractionated samples to be eventually prepared in the preparative separation and fractionation unit 2. Therefore, the system can be flexibly controlled according to the purpose of the analysis. For example, when there is an adequate amount of time available for the analytical measurement, the threshold can be set at a comparatively low level to increase the number of fractionated samples (i.e. to perform the preparative separation and fractionation in such a manner that some substances which are less useful than the substance having the highest degree of usefulness will also be additionally contained in the fractionated samples). Conversely, when the amount of time available for the analytical measurement is considerably limited, the threshold can be set at a high level to decrease the number of fractionated samples (i.e. to perform the preparative separation and fractionation in such a manner that only the substance having the highest degree of usefulness or a small number of substances having particularly high degrees of usefulness will be contained in the fractionated samples).

In the previous embodiment, the eluate which exits the column during the period of time which has been judged to be "useless" is disposed and completely excluded from the fractionated samples to be eventually analyzed. As another possibility, the timing of preparative separation and fractionation in the LCs 11 and 12 or the preparative separation and fractionation unit 2 may be controlled so that a shorter duration of fractionation is set within a period of time which has been judged to be "useful" while a longer duration of fractionation is set within a period of time which has been judged to be "useless." Increasing the duration of fractionation is likely to increase the number of substances to be contained in one fractionated sample, which makes the mass spectrum tend to be more complex and less accurate. However, such a deterioration in accuracy or sensitivity is allowable as long as the substances concerned are originally less useful. On the other hand, the substances with high degrees of usefulness are preparative-separated and fractionated with a shorter duration of fractionation, which means that each fractionated sample is likely to contain only one or a small number of substances, so that a high-quality mass spectrum can be obtained with high accuracy. The use of a longer duration of fractionation within the period of time which has been judged to be "useless" leads to a decrease in the total number of fractionated samples. Thus, the effect of shortening the analytical measurement time and reducing the amount of data can be obtained as in the previous embodiment.

The system in which the duration of fractionation is changed in the previously described manner can also be configured so that the fractionated sample usefulness information is expressed as multi-value information and the duration of fractionation is finely changed according to the usefulness value.

In the previous embodiment, a MALDI-MS is used as the MS unit 3. A mass spectrometer employing a laser desorption/ionization (LDI) method different from MALDI, a desorption electrospray ionization (DESI) method or other ionization methods can also be similarly used. The present invention cannot only be applied in a mass spectrometer which performs an analysis on fractionated samples prepared on a sample plate, but also in a mass spectrometer in which a liquid sample which has been preparative-separated and fractionated is ionized and analyzed directly (i.e. in the form of liquid) as in the case of a mass spectrometer using electrospray ionization (ESI) or atmospheric pressure chemical ionization (APCI).

It should be noted that the previous embodiment is a mere example of the present invention, and any change, addition or modification appropriately made within the spirit of the present invention will naturally fall within the scope of claims of the present patent application.

REFERENCE SIGNS LIST

1 . . . LC Unit
11 . . . First LC
12 . . . Second LC
2 . . . Preparative Separation and Fractionation Unit
3 . . . Mass Spectrometer (MS) Unit
4 . . . Data Processor Unit
5 . . . Analysis Control Unit
51 . . . Fractionated Sample Usefulness Information Memory
52 . . . Useful Fractionated Sample Selector
6 . . . Input Unit

The invention claimed is:

1. A method to perform liquid chromatography and mass spectrometry by a liquid chromatograph and a mass spectrometer, the method comprising:
   separating various substances contained in a sample according to their retention times to provide an eluate;
   fractionating the eluate from the liquid chromatograph at a preset interval of time, dropping the eluate into a plurality of wells, and obtaining a plurality of fractionated samples corresponding to the plurality of wells, respectively;
   ionizing and performing the mass spectrometry for each of the plurality of fractionated samples;
   storing a plurality of analysis conditions of the liquid chromatograph and the mass spectrometer and a fractionated sample usefulness information corresponding to each of the plurality of analysis conditions, which includes information of a temporal change of a plurality of index values representing a degree of usefulness with respect to a retention time, a degree of usefulness representing ease of ionization including a degree of hydrophilicity, a degree of acidity, and a molecular weight in an ion source of the mass spectrometer and analytical sensitivity, and includes an information of a time when a substance with high degree of usefulness is eluted from the liquid chromatograph;

setting one of the plurality of analysis conditions;

retrieving the stored fractionated sample usefulness information corresponding to the analysis condition set; and controlling the fractionating the eluate from the liquid chromatograph based on the degree of usefulness, so that only substances with high degrees of usefulness are contained in the plurality of fractionated samples.

2. The method according to claim 1, wherein:

the liquid chromatograph is a multi-dimensional liquid chromatograph capable of multi-dimensional separation and fractionation, the fractionated sample usefulness information is prepared for each dimension of the liquid chromatograph, and wherein the fractionating operation is controlled based on the fractionated sample usefulness information corresponding to the analysis condition so that substances with high degrees of usefulness are contained in the fractionated samples prepared at each dimension of the liquid chromatograph while preventing substances with relatively low degrees of usefulness from being contained in any of the fractionated samples.

3. The method according to claim 1, wherein:

the mass spectrometer is a MALDI mass spectrometer for performing a mass spectrometry on each of the fractionated samples separately prepared in wells formed on a sample plate.

4. The method according to claim 2, wherein:

the mass spectrometer is a MALDI mass spectrometer for performing a mass spectrometry on each of the fractionated samples separately prepared in wells formed on a sample plate.

5. A method to perform liquid chromatography and mass spectrometry by a liquid chromatograph and a mass spectrometer, the method comprising:

temporally separating various substances contained in a sample according to their retention times to provide an eluate;

fractionating the eluate from the liquid chromatograph at a preset interval of time, dropping the eluate into a plurality of wells, and obtaining a plurality of fractionated samples corresponding to the plurality of wells, respectively;

ionizing and performing the mass spectrometry for each of the plurality of fractionated samples;

storing a plurality of analysis conditions of the liquid chromatograph and the mass spectrometer and a fractionated sample usefulness information corresponding to each of the plurality of analysis conditions, which includes information of a temporal change of a plurality of index values representing a degree of usefulness with respect to a retention time, a degree of usefulness representing ease of ionization including a degree of hydrophilicity, a degree of acidity, and a molecular weight in an ion source of the mass spectrometer and analytical sensitivity, and includes an information of a time when a substance with high degree of usefulness is eluted from the liquid chromatograph;

setting one of the plurality of analysis condition;

retrieving the stored fractionated sample usefulness information corresponding to the analysis condition set; and controlling fractionating the eluate from the liquid chromatograph so as to change a duration of fractionation based on the degree of usefulness.

6. The method according to claim 5, wherein:

the liquid chromatograph is a multi-dimensional liquid chromatograph capable of multi-dimensional separation and fractionation, the fractionated sample usefulness information is prepared for each dimension of the liquid chromatograph, and wherein the fractionating operation is controlled based on the fractionated sample usefulness information so that the duration of fractionation for substances with high degrees of usefulness is decreased compared with the duration of fractionation for substances with relatively low degrees of usefulness in each dimension of the liquid chromatograph.

7. The method according to claim 5, wherein:

the mass spectrometer is a MALDI mass spectrometer for performing a mass spectrometry on each of the fractionated samples separately prepared in wells formed on a sample plate.

8. The method according to claim 6, wherein:

the mass spectrometer is a MALDI mass spectrometer for performing a mass spectrometry on each of the fractionated samples separately prepared in wells formed on a sample plate.

* * * * *